United States Patent
Eccleston et al.

(10) Patent No.: US 10,746,746 B2
(45) Date of Patent: Aug. 18, 2020

(54) METHOD FOR THE ENRICHMENT OF CELL FREE NUCLEOSOMES

(71) Applicant: BELGIAN VOLITION SPRL, Isnes (BE)

(72) Inventors: Mark Edward Eccleston, Isnes (BE); Jacob Vincent Micallef, Isnes (BE)

(73) Assignee: Belgian Volition SPRL, Isnes (BE)

( * ) Notice: Subject to any disclaimer, the term of this patent is extended or adjusted under 35 U.S.C. 154(b) by 162 days.

(21) Appl. No.: 15/768,984

(22) PCT Filed: Oct. 21, 2016

(86) PCT No.: PCT/GB2016/053305
§ 371 (c)(1),
(2) Date: Apr. 17, 2018

(87) PCT Pub. No.: WO2017/068371
PCT Pub. Date: Apr. 27, 2017

(65) Prior Publication Data
US 2019/0064184 A1    Feb. 28, 2019

(30) Foreign Application Priority Data

Oct. 21, 2015 (GB) .................................. 1518665.3

(51) Int. Cl.
| | | |
|---|---|---|
| *G01N 33/68* | (2006.01) | |
| *G01N 33/574* | (2006.01) | |
| *G01N 33/53* | (2006.01) | |
| *C12Q 1/6886* | (2018.01) | |

(52) U.S. Cl.
CPC ....... *G01N 33/6875* (2013.01); *C12Q 1/6886* (2013.01); *G01N 33/57488* (2013.01)

(58) Field of Classification Search
None
See application file for complete search history.

(56) References Cited

U.S. PATENT DOCUMENTS

| | | |
|---|---|---|
| 2011/0105353 A1 | 5/2011 | Lo et al. |
| 2013/0065254 A1 | 3/2013 | Lunyak |
| 2013/0230858 A1 | 9/2013 | Cantor et al. |

FOREIGN PATENT DOCUMENTS

| | | |
|---|---|---|
| EP | 0611080 A1 | 8/1994 |
| WO | WO-2011/092715 A2 | 8/2011 |

OTHER PUBLICATIONS

Jung et al. Molecular & Cellular Proteomics 9.5 year 2010 p. 838-850 (Year: 2010).*
Karczmarski et al. Clinical Proteomics 2014 p. 11:24 (Year: 2014).*
Lennartsson et al. 2009 vol. 1790: 863-868 (Year: 2009).*
Deligezer et al., "Sequence-Specific Histone Methylation Is Detectable on Circulating Nucleosomes in Plasma", Clinical Chemistry, 2008, 54(7):1125-1131.
Fujiya et al., "Nucleosomal DNA hypermethylation detected in sera of colon cancer patients as a marker of cancer surveillance", Digest Dis. Week Abs., 2003, Abstract No. W1331. (2 pages).
Holdenreider et al., "Nucleosomes in Serum of Patients With Benign and Malignant Diseases", Int. J. Cancer, 2001, 95:114-120.
Lo et al., "Maternal Plasma DNA Sequencing Reveals the Genome-Wide Genetic and Mutational Profile of the Fetus", Sci. Transl. Med., 2(61):61ra91. (15 pages), 2010.
Milne et al., "Chromatin Immunoprecipitation (ChIP) for Analysis of Histone Modifications and Chromatin-Associated Proteins", Methods in Molecular Biology, 2009, 538:409-423.
Sakamoto et al., "Immunoprecipitation of nucleosomal DNA is a novel procedure to improve the sensitivity of serum screening for the p16 hypermethylation associate with colon cancer", Cancer Epidemiology, 2010, 34(2):194-199.
Scaffidi, Paola, "Histone H1 alterations in cancer", Biochemica et Biophysica Acta, 2016, 1859(3):533-539.

* cited by examiner

*Primary Examiner* — Changhwa J Cheu
(74) *Attorney, Agent, or Firm* — McDermott, Will & Emery LLP; Judy M. Mohr

(57) ABSTRACT

The present invention relates to the use of a histone H1 binding agent for detecting, isolating and/or purifying cell free nucleosomes of tumor origin from a biological sample. The invention also describes methods of negative or positive selection using histone H1 binding agents, in order to enrich a sample for cell free nucleosomes of tumor origin.

20 Claims, 1 Drawing Sheet

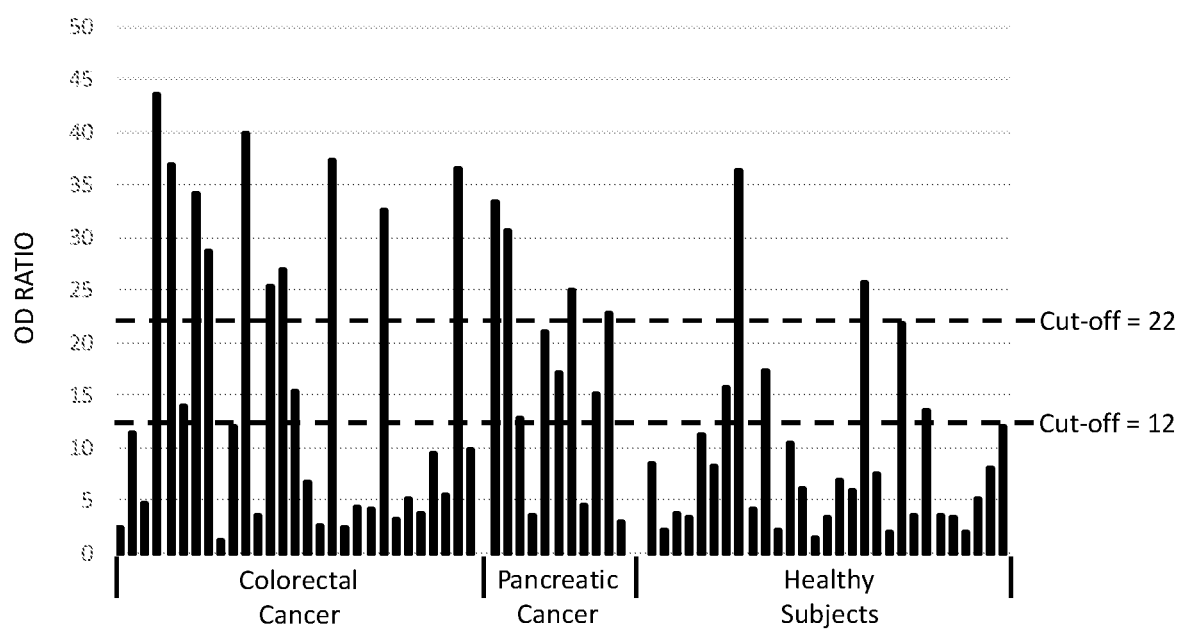

METHOD FOR THE ENRICHMENT OF CELL FREE NUCLEOSOMES

CROSS-REFERENCE TO RELATED APPLICATIONS

This application is a U.S. National Stage Application of PCT/GB2016/053305, filed Oct. 21, 2016, which claims the benefit of and priority to GB Patent Application No. GB 1518665.3 filed Oct. 21, 2015, the entire contents of each of which is incorporated herein by reference.

FIELD OF THE INVENTION

The invention relates to a method for the purification or enrichment of cell free nucleosomes of tumor origin and associated tumor DNA from blood, serum or plasma.

BACKGROUND OF THE INVENTION

Cellular DNA exists as a protein-nucleic acid complex called chromatin. The nucleosome is the basic unit of chromatin structure and consists of double stranded DNA (dsDNA) wound around a protein complex. The DNA is wound around consecutive nucleosomes in a structure often said to resemble "beads on a string" and this forms the basic structure of open or euchromatin. In compacted or heterochromatin this string is coiled and super coiled in a closed and complex structure.

Each nucleosome in chromatin consists of a protein complex of eight highly conserved core histones (comprising of a pair of each of the histones H2A, H2B, H3, and H4). Around this complex are wrapped approximately 146 base pairs (bp) of DNA. Another histone, H1 or H5, which is located on the nucleosome outside of the core histones, acts as a linker and is involved in chromatin compaction. Cell free nucleosomes are reported to comprise predominantly mono-nucleosomes together with associated DNA produced as chromatin fragments by digestion of chromatin on cell death.

Normal cell turnover in adult humans involves the creation by cell division of some $10^{11}$ cells daily and the death of a similar number, mainly by apoptosis. During the process of apoptosis chromatin is broken down into mononucleosomes and oligonucleosomes some of which may be found in the circulation. Under normal conditions the level of circulating nucleosomes found in healthy subjects is reported to be low. Elevated levels are found in subjects with a variety of conditions including many cancers, auto-immune diseases, inflammatory conditions, stroke and myocardial infarction (Holdenreider & Stieber, 2009). Nucleosomes from dead cells may also be shed into other body fluids such as urine, feces, or sputum.

DNA abnormalities are characteristic of all cancer diseases. The DNA of cancer cells differs from that of healthy cells in many ways including, but not limited to, point mutations, translocations, gene copy number, micro-satellite abnormalities, DNA strand integrity and nucleotide modifications (for example methylation of cytosine at position 5). These tumor associated alterations in DNA structure or sequence are investigated routinely in cancer cells or tissue removed at biopsy or surgery for clinical diagnostic, prognostic and treatment selection purposes. Tumor genetic and epigenetic characteristics vary between different tumor types and between different patients with the same tumor disease. Moreover, these characteristics vary over time within the same cancer of the same patient with the progression of the disease and in the development of acquired resistance to drug or other therapies. Thus serial investigation of tumor DNA in cells removed at surgery or biopsy may help the clinician to monitor disease progression and detect any relapse or acquired treatment resistance at an early stage (possibly many months earlier than radiological detection) and allow potentially successful changes in treatment courses.

However, tissue DNA tests have limitations as invasive biopsy procedures cannot be performed repeatedly on patients for monitoring purposes. For some patients, biopsy may not be used at all. Biopsy is expensive to perform, uncomfortable for the patient, poses patient risk, and may lead to surgical complications. Moreover, a tumor in a patient may consist of multiple tumoral clones located within different areas of the same tumor or within different metastases (in metastatic cancer) not all of which may be sampled on biopsy. A tissue biopsy DNA investigation therefore provides a snap-shot of the tumor, both in time and in space, amongst different tumor clones located within different areas of a tumor at a particular moment in time.

The blood of cancer patients contains circulating tumor DNA (ctDNA) which is thought to originate from the release of chromatin fragments or nucleosomes into the circulation from dying or dead cancer cells. Investigation of matched blood and tissue samples from cancer patients shows that cancer associated mutations, present in a patient's tumor (but not in his/her healthy cells) are also present in ctDNA in blood samples taken from the same patient (Newman et al, 2014). Similarly, DNA sequences that are differentially methylated (epigenetically altered by methylation of cytosine residues) in cancer cells can also be detected as methylated sequences in ctDNA in the circulation. In addition, the proportion of cell-free circulating DNA (cfDNA) that is comprised of ctDNA is related to tumor burden so disease progression may be monitored both quantitatively by the proportion of ctDNA present and qualitatively by its genetic and/or epigenetic composition. Analysis of ctDNA can produce highly useful and clinically accurate data pertaining to DNA originating from all or many different clones within the tumor and which hence integrates the tumor clones spatially. Moreover, repeated sampling over time is a much more practical and economic option. Analysis of (ctDNA) has the potential to revolutionize the detection and monitoring of tumors, as well as the detection of relapse and acquired drug resistance at an early stage for selection of treatments for tumors through the investigation of tumor DNA without invasive tissue biopsy procedures. Such ctDNA tests may be used to investigate all types of cancer associated DNA abnormalities (e.g.; point mutations, nucleotide modification status, translocations, gene copy number, micro-satellite abnormalities and DNA strand integrity) and would have applicability for routine cancer screening, regular and more frequent monitoring and regular checking of optimal treatment regimens (Zhou et al, 2012).

Blood, plasma or serum may be used as a substrate for ctDNA assays and any DNA analysis method may be employed including, without limitation, DNA sequencing, epigenetic DNA sequencing analysis (e.g., for sequences containing 5-methylcytosine), PCR, BEAMing, NGS (targeted or whole genome), digital PCR, cold PCR (co-amplification at lower denaturation temperature-PCR), MAP (MIDI-Activated Pyrophosphorolysis), PARE (personalized analysis of rearranged ends) and Mass Spectrometry.

As DNA abnormalities are characteristic of all cancer diseases and ctDNA has been observed for all cancer diseases in which it has been investigated, ctDNA tests have applicability in all cancer diseases. Cancers investigated include, without limitation, cancer of the bladder, breast, colorectal, melanoma, ovary, prostate, lung liver, endometrial, ovarian, lymphoma, oral, leukaemias, head and neck, and osteosarcoma (Crowley et al, 2013; Zhou et al, 2012; Jung et al, 2010). The nature of ctDNA tests will now be illustrated by outlining three (non-limiting) example approaches.

The first example involves the detection of a cancer associated gene sequence mutation in ctDNA. Blood tests involving the detection of a single gene mutation in ctDNA generally have low clinical sensitivity. There are two reasons for this. Firstly, although all cancers have mutations, the frequency of any particular mutation in a particular cancer disease is usually low. For example, although K-ras and p53 mutations are regarded as two of the more frequent cancer mutations and have been studied in a wide range of cancers including bladder, breast, colon, lung, liver, pancreas, endometrial and ovarian cancers, they were detected in 23%-64% and 17%-54% of cancer tissue samples respectively. Secondly, even if the cancer tissue of a patient does contain the mutation, the level or concentration of mutated ctDNA present in the blood of the patient may be low and difficult to detect. For example, K-ras and p53 mutations could be detected in the ctDNA of 0%-75% of K-ras and p53 tissue positive patients. The sum of these two effects meant that K-ras or p53 mutations were detected in the blood of less than 40% of cancer patients (Jung et al, 2010).

The second example involves the detection of multiple cancer associated gene sequence mutations in ctDNA. Although mutations of any particular gene such as K-ras or p53 may be present in only a minority of cancers, all cancers contain mutations so study of a sufficiently large panel of mutations should in principle, facilitate the detection of most or even all tumors. One way to increase the clinical sensitivity of such tests is therefore to test for a wide range of mutations in many genes. Newman et al have taken this approach for non-small cell lung cancer (NSCLC) and investigated 521 exons and 13 intron sequences from 139 recurrently mutated genes. The mutations studied encompassed multiple classes of cancer associated genetic alterations, including single nucleotide variation (SNV) and fusion genes. In this way the authors reported the detection of more than 95% of stage II-IV tumors and 50% of stage I tumors with 96% specificity in ctDNA blood tests (Newman et al, 2014).

The third example involves the detection of cancer associated epigenetic alterations to particular gene sequences in ctDNA. This approach can be applied to any DNA or nucleotide modification. A prime example of this approach is the detection of genes which are differentially methylated at cytosine residues in certain cancers. A large number of genes have been investigated for this purpose in a variety of cancers. A few of these are SEPTIN-9, APC, DAPK, GSTP1, MGMT, p16, RASSF1A, T1G1, BRCA1, ERα, PRB, TMS1, MLH1, HLTF, CDKN2A, SOCS1, SOCS2, PAXS, PGR, PTGS2 and RARβ2 investigated in bladder, breast, colorectal, melanoma, ovarian and prostate cancers. An illustrative example of this approach is the detection of methylated SEPTIN-9 in ctDNA for the detection of Col-oRectal Cancer (CRC) which was reported to detect 68% of CRC cases with a clinical specificity of 89% (Grutzmann et al, 2008).

The tumor derived ctDNA fraction of cfDNA circulates as small DNA fragments less than 200 bp in length consistent with that expected for DNA fragments circulating in the form of mono-nucleosomes (Newman et al, 2014). Cancer patients are reported to have higher cfDNA levels than healthy subjects. Workers in the field have reported ranges of 0-100 ng/ml (mean 30 ng/ml) cfDNA for healthy subjects and 0-1000 ng/ml (mean 180 ng/ml) cfDNA for subjects with cancer (Schwarzenbach et al, 2011). Circulating cfDNA consists of DNA molecules of various sizes up to 20,000 base pairs in length (Zhou et al, 2012). In agreement with the hypothesis that ctDNA circulates predominantly as mono-nucleosomes, measured levels of cell free nucleosomes in the circulation are, like DNA levels, higher in cancer patients than in healthy subjects (Holdenrieder et al, 2001). However, raised levels of circulating nucleosomes per se are not used clinically as biomarkers of cancer as nucleosomes are a non-specific product of cell death and raised levels are observed for many conditions involving elevated cell death including acute trauma (Holdenrieder and Stieber, 2009). As a product of cell death, circulating nucleosome levels can rise markedly on treatment with cytotoxic drugs or radiotherapy. However, nucleosomes are also cleared from the circulation so levels may spike with treatment and then fall (Holdenrieder et al, 2001).

Although the level of circulating cell free nucleosomes per se has not been used in clinical practice as a blood based biomarker in cancer, the epigenetic composition of circulating cell free nucleosomes in terms of their histone modification, histone variant, DNA modification and adduct content have been investigated as blood based biomarkers in cancer (WO 2005/019826; WO 2013/030577; WO 2013/030579; WO 2013/084002).

The biological origin of cfDNA is not well understood. Fragmentation of chromatin to produce mononucleosomes and oligonucleosomes is a feature of apoptotic cell death. Necrotic cells are thought to produce larger DNA molecules of thousands of base pairs in length, but DNA fragmentation may also occur in some cases of necrosis. Further, common DNA repeat sequences (e.g.; ALU or LINE1 sequences) may be released as 200-400 base pair DNA fragments from cells undergoing non-apoptotic or necrotic cell death (Schwarzenbach et al, 2011). DNA fragments may also be secreted by cells as a form of inter-cellular communication. The origin of ctDNA is thought to be related to the death of cancer cells. DNA fragments may be released as nucleosomes from necrotic and/or apoptotic tumor cells. However, necrotic and apoptotic cells are usually phagocytosed by macrophages or other scavenger cells and DNA may be released by macrophages that have engulfed necrotic or apoptotic cells (Schwarzenbach et al, 2011).

There are a variety of methods available for extracting cfDNA from blood, serum or plasma and these have been compared for yield of extracted DNA and for their efficiency of extraction of DNA fragments of different lengths. Phenol-chloroform and sodium iodide extraction methods provide the highest yield and extract small DNA fragments of less than 200 bp in length. Other methods tested (including commercially available methods) are reported to have lower DNA extraction yields and to fail to extract small DNA fragments of less than 200 bp in length (Fong et al, 2009).

Extraction of cfDNA from blood, serum or plasma for analysis of ctDNA is usually performed using commercially available DNA extraction products. Such extraction methods claim high recoveries of circulating DNA (>50%) and some products (for example; the QIAamp Circulating Nucleic Acid Kit produced by Qiagen) are claimed to extract DNA fragments of small size. Typical sample volumes used are in the range 1-5 mL of serum or plasma.

There are currently no ctDNA based tests in routine use for clinical oncology purposes due to a number of limitations. A major methodological limitation is a requirement for high quality DNA. Current ctDNA sampling methods produce poor quality ctDNA samples due to the nature of the sample. The main difficulty lies in the presence of large amounts of non-tumor cfDNA in the circulation which complicates any analysis of ctDNA. Estimates from different workers vary but the fraction of ctDNA present in the circulation can be too low to detect or above 50% of cfDNA. However, for most cancer patients the ctDNA fraction is a small part of cfDNA. For example, recent studies report that the ctDNA fraction increases with tumor size in pre-treatment lung cancer patients. The highest level found was 3.2% in a patient with a large tumor burden but most patients were found to have ctDNA fractions below 0.1% (Newman et al, 2014). This means that for many patient samples, a very low level of ctDNA must be analysed in the presence of a much higher level of non-tumor derived DNA. Moreover, this DNA is from the same subject and hence of similar sequence and will interfere in any method for the quantification or analysis of ctDNA.

A similar problem occurs for the measurement of circulating cell free nucleosomes and/or the epigenetic composition of circulating nucleosomes as biomarkers for cancer because nucleosomes per se are a non-specific indicator of cell death and are released as part of the normal cell turnover process of the body as well as in conditions associated with elevated levels of cell death such as autoimmune diseases, stroke, sepsis, post trauma, burns, myocardial infarction, cerebral stroke, during graft rejection after organ transplantation and after severe exercise. Thus nucleosomes of tumor origin circulate together with other non-tumor nucleosomes of various cellular and tissue origins. These non-tumor nucleosomes will interfere in any method for the quantification or epigenetic analysis of nucleosomes of tumor origin. A similar effect may occur in other body fluids. Feces, for example, may contain nucleosomes and associated DNA of colorectal cancer cell origin together with nucleosomes originating in healthy colon or rectal cells. Sputum may contain nucleosomes and associated DNA of lung cancer cell origin together with nucleosomes originating in healthy lung cells. Similar effects will occur in other body fluids.

There is therefore a great need for a method for the enrichment of nucleosomes and DNA of tumor origin from blood, serum or plasma samples and other body fluid samples. Similarly, there is a need for analytical methods for circulating cell free nucleosomes which are able to distinguish those nucleosomes of tumor and non-tumor origin for improved detection of cancer disease states.

SUMMARY OF THE INVENTION

According to a first aspect of the invention, there is provided a method for analysing cell free nucleosomes of tumor origin from a biological sample by affinity purification wherein said method comprises the steps of:
  (i) contacting the sample with a histone H1 binding agent;
  (ii) isolating nucleosomes from the sample which are not bound to the histone H1 binding agent; and
  (iii) analysing the isolated nucleosomes by immunoassay or mass spectroscopy.

According to a further aspect of the invention, there is provided a method for isolating purified tumor DNA from a biological sample, wherein said method comprises the steps of:
  (i) contacting the sample with a histone H1 binding agent;
  (ii) isolating nucleosomes which are not bound to the histone H1 binding agent;
  (iii) extracting DNA from the nucleosome sample isolated in step (ii); and
  (iv) analysing the extracted DNA.

According to a further aspect of the invention, there is provided an immunoassay method for detecting an epigenetic epitope of tumor derived nucleosomes in a biological sample, wherein said method comprises the steps of:
  (i) contacting the sample with a first binding agent comprising a histone H1 binding agent;
  (ii) isolating nucleosomes which are not bound to the first binding agent;
  (iii) contacting the nucleosomes with a second binding agent which binds to said epitope;
  (iv) detecting and/or quantifying the binding of said second binding agent to said epitope; and
  (v) using the presence or degree of such binding as a measure of the presence of the particular epitope of tumor derived nucleosomes in the sample.

According to a further aspect of the invention, there is provided a method for detecting cancer in an animal or a human subject which comprises the steps of:
  (i) obtaining a biological sample from the subject;
  (ii) analyzing the sample for cell free nucleosomes that contain an epigenetic feature and also contain histone H1 by means of an immunoassay using two binding agents, one of which is directed to bind to the particular epigenetic feature and the other of which is directed to bind to histone H1;
  (iii) analyzing the sample for circulating cell free nucleosomes that contain the particular epigenetic feature, both with and without histone H1, by means of an immunoassay using two binding agents, one of which is directed to bind to the epigenetic feature and the other of which is directed to bind to a common core nucleosome epitope including any histone H2, H3 or H4 epitope, any DNA epitope or any other epitope present in chromatin fragments other than a histone H1 epitope; and
  (iv) using a combination of the immunoassay results obtained in steps (ii) and (iii) as a combination biomarker indicative of the presence of said cancer in the subject.

According to a further aspect of the invention, there is provided the use of a histone H1 binding agent for detecting, isolating and/or purifying cell free nucleosomes of tumor origin from a biological sample.

According to a further aspect of the invention, there is provided the use of a kit comprising a histone H1 binding agent in a method described herein.

BRIEF DESCRIPTION OF THE FIGURES

FIG. 1: OD Ratios (OD2:OD1) indicating relative proportions of [tumor derived and non-tumor derived nucleosomes]:[predominantly non-tumor derived nucleosomes] for 69 human subjects.

DETAILED DESCRIPTION OF THE INVENTION

The structure of nucleosomes in terms of their epigenetic signal composition may vary in cancer cells compared to healthy cells. The use of antibodies or other binders directed to bind to epigenetic signals that are more common in cancer cells than healthy cells or vice versa allows for the isolation of cell free nucleosomes of tumor origin (i.e. by positive or negative selection) in a biological sample taken from a subject which contains cell free nucleosomes with a mixture of cellular origins.

The nucleosome core consists of 8 histone proteins including a pair each of H2A, H2B, H3 and H4 histone proteins. Histone H1 (H1) is not a core histone but is located on the outside of the core and acts as a linker. In particular, H1 is involved with the packing of the "beads on a string" sub-structures into a high order structure. Without being bound by theory, the present inventors have identified that cell free nucleosomes originating from a tumor less frequently contain histone H1 than nucleosomes originating in healthy cells. Nucleosomes of tumor origin are more likely therefore to consist only of the 8 core histone proteins H2A, H2B, H3 and H4 (plus DNA and any adducted molecules). Circulating cell free nucleosomes in the blood which have a tumor or non-tumor origin can thus be considered to be qualitatively different in that most nucleosomes of tumor origin comprise a core nucleosome structure of 8 histone proteins together with an associated fragment of DNA, whilst most nucleosomes of non-tumor origin comprise a similar core nucleosome structure plus an additional histone H1 protein moiety and an associated fragment of DNA. This qualitative difference can be used as the basis of a negative selection method for the enrichment of cell free nucleosomes of tumor origin in a body fluid sample collected from a subject or patient.

We have previously reported methods for the epigenetic analysis of cell free nucleosomes in blood and other body fluids (WO2013/030577, WO2013/030578, WO2013/030579, WO2013/084002). As discussed above, cell free nucleosomes of tumor origin are released into the circulation of subjects with a tumor, but these are diluted into cell free nucleosomes already present in the circulation due to normal cell turnover. Any such nucleosomes of non-tumor origin will interfere in the genetic or epigenetic analysis of tumor nucleosomes. Removal of cell free nucleosomes of non-tumor origin from a body fluid sample will lead to higher purity of cell free nucleosomes of tumor origin leading to improved results for the genetic or epigenetic analysis of tumor nucleosomes or chromatin fragments in the sample.

In a preferred aspect of the invention circulating cell free nucleosomes of disease origin are purified and analysed for epigenetic features by immunoassay or mass spectroscopy. In this aspect; a blood, serum, plasma or other body fluid sample is taken from a subject and the sample is enriched for cell free nucleosomes of disease origin by removal of cell free nucleosomes containing a Histone H1 component. The remaining cell free nucleosomes are analysed for an epigenetic feature which is indicative of disease using an immunoassay or mass spectrophotometric method. The epigenetic nucleosome features that may be analysed include any or all of; particular histone post-translational modifications, particular histone isoforms, particular nucleotides or modified nucleotides (for example methylated, hydroxyl-methylated or other nucleotide modifications). Advantages of immunoassay and mass spectroscopy methods include low cost, high analytical sensitivity and specificity and high throughput.

In one embodiment there is provided a method for the isolation by affinity purification and epigenetic analysis of cell free nucleosomes of disease origin from a biological sample wherein said method comprises the steps of:
(i) contacting the sample with a histone H1 binding agent;
(ii) isolating nucleosomes from the sample which are not bound to the histone H1 binding agent (i.e. unbound nucleosomes); and
(iii) analysing the isolated nucleosome fraction for inclusion of a modified nucleotide using an immunoassay method involving an antibody or other binder directed to bind to a modified nucleotide.

In another embodiment there is provided a method for the isolation by affinity purification and epigenetic analysis of cell free nucleosomes of disease origin from a biological sample wherein said method comprises the steps of:
(i) contacting the sample with a histone H1 binding agent;
(ii) isolating nucleosomes from the sample which are not bound to the histone H1 binding agent (i.e. unbound nucleosomes); and
(iii) analysing the isolated nucleosome fraction for inclusion of post translationally modified histone using an immunoassay method involving an antibody or other binder directed to bind to a post translationally modified histone.

In a further embodiment there is provided a method for the isolation by affinity purification and epigenetic analysis of cell free nucleosomes of disease origin from a biological sample wherein said method comprises the steps of:
(i) contacting the sample with a histone H1 binding agent;
(ii) isolating nucleosomes from the sample which are not bound to the histone H1 binding agent (i.e. unbound nucleosomes); and
(iii) analysing the isolated nucleosome fraction for inclusion of a histone isoform using an immunoassay method involving an antibody or other binder directed to bind to a histone isoform.

In a further embodiment there is provided a method for the isolation by affinity purification and epigenetic analysis of cell free nucleosomes of disease origin from a biological sample wherein said method comprises the steps of:
(i) contacting the sample with a histone H1 binding agent;
(ii) isolating nucleosomes from the sample which are not bound to the histone H1 binding agent (i.e. unbound nucleosomes); and
(iii) analysing the isolated nucleosome fraction for attachment to an adducted non-histone protein using an immunoassay method involving an antibody or other binder directed to bind to a non-histone protein.

In a further embodiment there is provided a method for the isolation by affinity purification and detection of cell free nucleosomes of disease origin from a biological sample taken from a patient wherein said method comprises the steps of:
(i) contacting the sample with a histone H1 binding agent;
(ii) isolating nucleosomes from the sample which are not bound to the histone H1 binding agent (i.e. unbound nucleosomes);
(iii) quantifying the isolated nucleosomes by immunoassay; and
(iv) using the presence or level of cell free nucleosomes not including a histone H1 moiety as an indicator of the disease state of the subject In a preferred analytical aspect of the invention, an epigenetic feature of circulating cell free nucleosomes present in a sample is analysed or measured in (i) nucleosomes that contain histone H1 and in (ii) all nucleosomes both with and without a histone H1. Measuring an epigenetic feature of nucleosomes that contain histone H1 (i.e. predominantly non-tumor nucleosomes) may be performed by methods known in the art including, without limitation, mass spectroscopy or by means of an immunoassay using two antibodies (or other binding agents), one of which is directed to bind to the epigenetic feature of interest and the other of which is directed to bind to histone H1. Direct measurement of an epigenetic feature of nucleosomes that do not contain histone H1 (i.e. predominantly tumor nucleosomes) is best performed following enrichment by removal of H1 associated nucleosomes using an affinity purification method as described herein. However, (all) circulating cell free nucleosomes, both with and without histone H1 (i.e. both tumor and non-tumor nucleosomes), may be analysed or measured by mass spectroscopy or by means of an immunoassay using two antibodies (or other binding agents), one of which is directed to bind to the epigenetic feature of interest and the other of which is directed to bind to a common core nucleosome epitope including any histone H2, H3 or H4 epitope, any DNA epitope or any other epitope present in chromatin fragments other than a histone H1 epitope. In this aspect of the invention, circulating cell free nucleosomes containing the epigenetic feature and also incorporating histone H1 can be measured (i.e. non-tumor nucleosomes), as well as all circulating cell free nucleosomes containing the epigenetic feature including both nucleosomes with and without histone H1 (i.e. both tumor and non-tumor nucleosomes). These two analyses or measurements can be used together as an indicator of the amount or proportion of circulating cell free nucleosomes present in a sample that contain the particular epigenetic feature that are not associated with histone H1. That is the amount or proportion of those nucleosomes that are likely to have a tumor origin. For example, the difference between the two measurements may be used or a ratio of the two measurements may be used.

In a preferred embodiment of this analytical aspect of the invention, there is provided a method for measuring the proportion of circulating cell free nucleosomes containing an epigenetic epitope in a biological sample taken from a subject that are of tumor origin, comprising the steps of;
(i) obtaining a body fluid sample from a subject,
(ii) performing a first immunoassay comprising the steps of;
  (1A) contacting the sample with a first binding agent which binds to said epigenetic epitope;
  (1B) contacting the nucleosomes or sample with a second binding agent which binds to histone H1; and
  (1C) detecting or quantifying the binding of said second binding agent to the nucleosome in the sample;
(iii) performing a second immunoassay comprising the steps of;
  (2A) contacting the sample with a first binding agent which binds to said epigenetic epitope;
  (2B) contacting the nucleosomes or sample with a third binding agent which binds to a non-histone H1 nucleosome or chromatin fragment epitope; and
  (2C) detecting or quantifying the binding of said third binding agent to the nucleosome in the sample;
(iv) combining the measurements of steps (1C) and (2C) as an indicator of the amount or proportion of cell free nucleosomes in the sample that contain said epigenetic epitope and that are of tumor origin.

In another embodiment of this analytical aspect of the invention, there is provided a method for measuring the proportion of circulating cell free nucleosomes, containing an epigenetic epitope in a biological sample taken from a subject that are of tumor origin, comprising the steps of;
(i) obtaining a body fluid sample from a subject,
(ii) performing a first immunoassay comprising the steps of;
  (1A) contacting the sample with a first binding agent which binds to histone H1;
  (1B) contacting the nucleosomes or sample with a second binding agent which binds to said epigenetic epitope; and
  (1C) detecting or quantifying the binding of said second binding agent to the nucleosome in the sample;
(iii) performing a second immunoassay comprising the steps of;
  (2A) contacting the sample with a first binding agent which binds to a non-histone H1 nucleosome or chromatin fragment epitope;
  (2B) contacting the nucleosomes or sample with a third binding agent which binds to said epigenetic epitope; and
  (2C) detecting or quantifying the binding of said third binding agent to the nucleosome in the sample;
(iv) combining the measurements of steps (1C) and (2C) as an indicator of the amount or proportion of cell free nucleosomes in the sample that contain said epigenetic epitope and that are of tumor origin.

It will be clear to those skilled in the art that the "first" and "second" immunoassays referred to above can be performed in any order or in parallel or in multiplex format. It will also be clear that the permutation of first and second, or first and third, binding agents used in the two immunoassays need not be symmetrical as described above.

In preferred embodiments the epigenetic epitope or feature is selected from (i) an isoform of histone H2, H3 or H4, (ii) a post translational modification present in histone H2, H3 or H4, (iii) a nucleotide including a modified nucleotide, (iv) a non-histone protein incorporated in or adducted to a cell free chromatin fragment. In a further embodiment the epigenetic epitope is a common epitope present in nucleosomes per se and the two immunoassays provide an indicator of the presence of tumor nucleosomes per se.

In a preferred embodiment of this aspect of the invention, the amount or proportion of cell free nucleosomes containing a particular epigenetic epitope that are of disease origin may be used as a biomarker for the presence of the disease in a subject or to assess a subject for disease status or suitability for a treatment regime.

We have successfully developed an analytical procedure as described above and in EXAMPLE 15, in which a non-histone protein nucleosome adduct was measured by two immunoassays and a ratio of: [nucleosomes per se containing the non-histone protein]:[nucleosomes containing histone H1 and the non-histone protein], was derived. Thus the ratio derived is an indicator of [all nucleosome-protein adducts]:[non-tumor nucleosome protein adducts]. Thus, for a blood, serum or plasma sample obtained from a subject, the larger the ratio derived for a sample the more probable that some of the nucleosomes have a tumor origin. In 29 healthy subjects the mean immunoassay output (Optical Density) ratio found was 8.7. In 29 subjects diagnosed with colorectal cancer the mean ratio was 15.9. In 11 subjects diagnosed with pancreatic cancer the mean ratio was 17.1. This demonstrates that an increasing ratio is indeed associated with nucleosomes of cancer origin.

Moreover, the individual results for each subject were used as a biomarker for cancer with increasing cut-off levels. At a cut-off of 12; the ratio gave a positive result for 73% (8 of 11) of subjects diagnosed with pancreatic cancer and 41% (12 of 29) of subjects diagnosed with colorectal cancer at a clinical specificity of 79% (6 false positive results among 29 healthy subjects). At a cut-off of 22; the ratio gave a positive result for 36% (4 of 11) of subjects diagnosed with pancreatic cancer and 34% (10 of 29) of subjects diagnosed with colorectal cancer at a clinical specificity of 93% (2 false positive results among 29 healthy subjects). These results demonstrate that the ratio described herein can be used as biomarker for cancer diseases.

It will be understood that references herein to "histone H1 binding agent" (e.g. in negative selection methods) refers generally to binding agents which bind to the histone H1 protein, including any histone H1 variants, isoforms, or modifications thereof. Therefore, in one embodiment the histone H1 binding agent is selected from: a binding agent that binds to histone H1 protein, variant, isoform or modification thereof.

In the above embodiments, the presence or level of enriched cell free nucleosomes of disease origin per se, or the presence or level of enriched cell free nucleosomes of disease origin containing a modified nucleotide, post-translational histone modification, histone isoform or nucleosome-protein adduct detected may be used as an indicator of disease status, disease prognosis, disease monitoring, treatment monitoring or disease susceptibility to particular treatments or for other clinical applications.

We have previously reported nucleosome immunoassay methods suitable for use in the present invention including the methods described in WO2005/019826, WO2013/030577, WO2013/030578, WO2013/030579, WO2013/084002. Without limitation, any of these methods may be employed in the present invention.

Furthermore, the inventors have identified that where nucleosomes originating from a tumor are associated with H1, the nucleosome associated H1 is subject to further modifications and/or may contain different H1 variants or H1 isoforms than those present in nucleosomes originating in healthy cells.

The main histone H1 variants or isoforms include, without limitation, H1.0, H1.10 and H1X which are expressed in proliferating and resting somatic cells as well as H1 variants H1.1, H1.2, H1.3, H1.4, H.1.5 and H1.6 which are expressed at high levels in dividing cells. In addition, there are germ line specific variants including H1.8 which is expressed mainly in the testis and H1.7 which is expressed mainly in the oocyte. The histone variant composition of chromatin is altered in cancer cells and it is reported that, of the common H1 isoforms, histone H1.0 isoform expression is down regulated in cancer cells whereas histone isoforms H1.1, H1.2, H1.3, H1.4 and H1.5 are expressed at high levels in cancer cells (Scaffidi; 2015).

Histone H1 may be post-translationally modified at amino acid residues located in the N- and C-terminal tails as well as within the globular domain of the protein and these modifications may be associated with cancer (Izzo and Schneider; 2015). It will be understood that reference herein to "histone H1 modifications" refer to H1 post-translational modifications (PTM) which may include acetylation, methylation, which may be mono-, di- or tri-methylation, phosphorylation, ubiquitination, ADP ribosylation, citrullination, hydroxylation, glycosylation, nitrosylation, glutamination and/or isomerisation. A histone amino acid residue having a modification may be any Ser, Lys, Arg, His, Glu, Pro or Thr residue within the histone amino acid sequence.

For example, a lysine residue within the core histone sequence may be mono-, di- or tri-methylated, acetylated or ubiquitinated, an arginine residue within the core histone sequence may be monomethylated, symmetrically or asymmetrically dimethylated or converted to citrulline, a serine or threonine residue within the core histone sequence may be phosphorylated and/or a proline residue within the core sequence may be isomerised.

It will be understood by a person skilled in the art that the notation used to describe a particular histone modification indicates which histone has been modified, the particular amino acid(s) that have been modified and the type of modification that has occurred. For example, H1K64(Ac) denotes the acetylation of histone H1 at lysine 64.

In one embodiment, the binder(s) used for the invention are directed to bind to a histone H1 modification associated with a cell free nucleosome. In a further embodiment, the histone H1 modification is selected from phosphorylation, acetylation, methylation, ubiquitination and/or formylation. H1 modifications may include: phosphorylation at sites S2, T4, T11, S/T18, S27, T31, S36, S37, T39, S41, S44, S107, T138, T142, T146, T147, T154, T155, T165, S172, S173, T180, S/T187, S189; acetylation at sites: S2, K17, K26, K34, K46, K49, K52, K63, K64, K85, K88, K90, K93, K97, K109, K168, K169, K192, K209; methylation at sites: K26, K27, K34, K52, K64, K97, K106, K119, K148, K168, K169, K187; ubiquitination at sites: K17, K21, K34, K46, K47, K64, K65, K75, K76, K85, K86, K90, K91, K97, K98, K106, K107; formylation at sites: K17, K34, K46, K63, K64, K67, K75, K85, K88, K90, K97, K110, K140, K141, K160. Therefore, in one embodiment, the histone H1 modification associated with a cell free nucleosome comprises at least one of the histone H1 modifications as listed herein.

In one embodiment, the binder(s) used for the invention is directed to bind to a histone H1 variant or isoform associated with a cell free nucleosome. H1 variants and isoforms may include H1.1, H1.2, H1.3, H1.4, H1.5 or H1.6 which are thought to be expressed during mitosis and H1.0, H1.10 and H1X which are expressed in resting somatic cells. Additional H1 variants have also been identified in specific tissues, such as variants H1t, H1T2, H1LS in the testis, as well as in specific cell types, such as variant H1.0 in terminally differentiated cells. Therefore, in one embodiment, the histone H1 variant or isoform associated with a cell free nucleosome comprises at least one of the histone H1 variants or isoforms as listed herein.

It will be clear to those skilled in the art that enrichment of biological samples taken from human or animal subjects patients for nucleosomes of tumor origin based on their quantitive H1 association or on their qualitative H1 isoform and/or H1 PTM modification composition would be likely to improve the discrimination of differential diagnosis using nucleosome or DNA biomarkers. Therefore, in one embodiment, the immunoseparation of nucleosomes of healthy or tumor origin utilises a binder directed to bind to at least one histone H1 modification and/or variant and/or isoform associated with a cell free nucleosome.

In one embodiment a biological fluid sample is taken from a subject and cell free nucleosomes in the sample are enriched for nucleosomes of a tumor origin on the basis of nucleosome histone H1 composition. The fluid sample may be any biological fluid sample taken from a subject including, without limitation, cerebrospinal fluid (CSF), whole blood, blood serum, plasma, menstrual blood, endometrial fluid, urine, saliva, or other bodily fluid (stool, tear fluid, synovial fluid, sputum), breath, e.g. as condensed breath, or an extract or purification therefrom, or dilution thereof. Biological samples also include specimens from a live subject, or taken post-mortem. The samples can be prepared, for example where appropriate diluted or concentrated, and stored in the usual manner.

In one embodiment, the cell free nucleosomes of tumor origin originate from a cancer selected from: breast cancer, bladder cancer, colorectal cancer, skin cancer (such as melanoma), ovarian cancer, prostate cancer, lung cancer, pancreatic cancer, bowel cancer, liver cancer, endometrial cancer, lymphoma, oral cancer, head and neck cancer, leukaemia and osteosarcoma.

In one embodiment, the nucleosome is a cell free mononucleosome or oligonucleosome.

Methods

Negative Selection

It will be clear to those skilled in the art that positive selection by affinity binding of cell free nucleosomes of tumor origin, in a blood sample containing nucleosomes of tumor cell and healthy cell origin, based on histone H1 isoform or histone H1 post translational modification pattern, is only possible where the cell free nucleosomes of tumor origin retain and include the H1 protein moiety. However, the majority of circulating cell free nucleosomes of tumor origin do not include an H1 moiety. For this reason; negative selection is the preferred method for enriching circulating cell free nucleosomes of tumor origin.

According to a first aspect of the invention, there is provided a method for isolating/analysing cell free nucleosomes of tumor origin from a biological sample by affinity purification wherein said method comprises the steps of:
  (i) contacting the sample with a histone H1 binding agent (including any histone H1 variants, isoforms, or modifications thereof);
  (ii) isolating nucleosomes from the sample which are not bound to the histone H1 binding agent (i.e. unbound nucleosomes); and
  (iii) analysing the isolated nucleosomes and/or associated DNA.

According to this aspect of the invention there is provided a method for enriching a biological sample for nucleosomes of tumor origin by negative selection of cell free nucleosomes containing a histone H1 protein, or one or more particular histone H1 variants, or one or more particular histone H1 modifications. In one embodiment an antibody or other binder directed to bind to histone H1 or histone H1 variants H1.0, H1.10 or H1X (or any binders directed to any combination of these) is used to select and isolate nucleosomes containing the H1 variant and thus bind to nucleosomes of healthy cell origin. This method thus removes nucleosomes of healthy cell origin from the sample which is hence enriched for nucleosomes of tumor origin. In a preferred embodiment the binder is an antibody immobilised on a solid phase for immunoextraction of nucleosomes of healthy origin. The nucleosomes and/or associated DNA remaining in the liquid phase may be analysed for genetic sequence, epigenetic signal structures or other characteristics.

Therefore, according to an aspect of the invention, there is provided a method for isolating/analysing cell free nucleosomes of tumor origin from a biological sample by affinity purification wherein said method comprises the steps of:
  (i) contacting the sample with a histone 1 binding agent that binds to histone H1 protein per se or a histone H1 variant selected from H1.0, H1.10 or H1.X;
  (ii) isolating nucleosomes from the sample which are not bound to the binding agent (i.e. unbound nucleosomes); and
  (iii) analysing the isolated nucleosomes and/or associated DNA.

In one embodiment, the isolated nucleosomes are analysed by immunoassay or mass spectroscopy. The level or amount of nucleosomes of tumor origin present and/or any molecular genetic or epigenetic characteristics of the nucleosomes of tumor origin may be used to detect cancer in a subject or to assess the cancer of a subject for any clinical purpose. In a further embodiment, the isolated nucleosomes are analysed by immunoassay or mass spectroscopy for inclusion of an epigenetic feature. In a yet further embodiment, the epigenetic feature comprises a post-translational histone modification, a histone isoform, a modified nucleotide or an adducted non-histone protein. In a further embodiment, the DNA component of the isolated nucleosomes is analysed for DNA base sequence.

References to "histone H1 protein" in the negative selection methods described herein include the native or wild-type histone H1 protein. As explained previously, cell free nucleosomes originating from a tumor less frequently contain histone H1 than nucleosomes originating in healthy cells, therefore this embodiment enables the isolation of cell free nucleosomes of tumor origin by detecting for the presence or absence of the native/wild-type histone H1 protein.

Positive Selection

In the present invention, positive selection methods are based on the use of affinity binding agents directed to bind to post translationally modified histone H1 protein molecules or to H1 protein isoforms that are associated with dividing or proliferating cells as described above. In particular, post translationally modified histone H1 protein binding targets for use in positive selection include any selected from those listed above. H1 isoforms for use in positive selection include a histone H1 isoform or variant selected from H1.1, H1.2, H1.3, H1.4, H.1.5 or H1.6, According to one aspect of the invention, there is provided a method for isolating/analysing cell free nucleosomes of tumor origin from a biological sample by affinity purification wherein said method comprises the steps of:
  (i) contacting the sample with a binding agent to a histone H1 variant, isoform, or a modification thereof which is prevalent in nucleosomes of cancer origin;
  (ii) isolating nucleosomes from the sample which are bound to the histone H1 binding agent; and
  (iii) analysing the isolated nucleosomes and/or associated DNA.

According to this aspect of the invention there is provided a method for enriching a biological sample for nucleosomes of tumor origin by positive selection of cell free nucleosomes containing a histone H1 protein, or one or more particular histone H1 variants, or one or more particular histone H1 modifications that are prevalent in nucleosomes of cancer origin. In a preferred embodiment an antibody or other binder directed to bind to H1 variant H1.1, H1.2, H1.3, H1.4, H1.5 or H1.6 (or any binders directed to bind to any combination of these) is used to select and isolate nucleosomes containing the H1 variant and thus enriching nucleosomes of tumor origin whilst many nucleosomes of healthy cell origin remain unbound and can be separated. In another preferred embodiment an antibody or other binder directed to bind to a H1 modification (or any binders directed to bind to a combination of modifications) is used to select and isolate nucleosomes containing the H1 modification and thus enriching nucleosomes of tumor origin whilst many nucleosomes of healthy cell origin remain unbound and can be separated. In a preferred embodiment the binder is an antibody immobilised on a solid phase for immunoextraction of nucleosomes of tumor origin. The nucleosomes and/or associated DNA bound to the solid phase may be analysed for genetic sequence, epigenetic signal structures or other characteristics.

Therefore, according to an aspect of the invention, there is provided a method for isolating/analysing cell free nucleosomes of tumor origin from a biological sample by affinity purification wherein said method comprises the steps of:
- (i) contacting the sample with a binding agent that binds to a histone H1 variant selected from H1.1, H1.2, H1.3, H1.4, H.1.5 or H1.6, or a histone H1 modification;
- (ii) isolating nucleosomes from the sample which are bound to the binding agent; and
- (iii) analysing the isolated nucleosomes and/or associated DNA.

In one embodiment, the isolated nucleosomes are analysed by immunoassay or mass spectroscopy. In a further embodiment, the isolated nucleosomes are analysed by immunoassay or mass spectroscopy for inclusion of an epigenetic feature. In a yet further embodiment, the epigenetic feature comprises a post-translational histone modification, a histone isoform, a modified nucleotide or an adducted non-histone protein. In a further embodiment, the DNA component of the isolated nucleosomes is analysed for DNA base sequence.

Cell free nucleosomes of tumor origin exist in biological fluids as part of a mixture of nucleosomes with a variety of origins and comprise only a proportion of the cell free nucleosomes present. Surprisingly it has been found that enrichment or isolation of nucleosomes of tumor origin may be performed by positive or negative selection using an affinity purification isolation method as described herein.

Circulating nucleosome levels can spike markedly 2-5 days after a sudden increase in cell death resulting from any number of disparate causes including trauma, stroke or treatment with cytotoxic drugs or radiotherapy. Levels then fall over a period of 2-3 days (Holdenrieder et al, 2001). This effect is due to induction of cell death followed by clearance from the circulation (Holdenrieder & Stieber, 2009).

It is clear that nucleosomes released into the circulation of patients with no tumor disease (including for example due to surgical trauma) cannot have a tumor origin. These nucleosomes will contribute to cfDNA but will not contain ctDNA.

It will be clear that the term "nucleosome" as used herein is intended to include mononucleosomes and oligonucleosomes and any such chromatin fragments that can be analysed in fluid media. In a further embodiment, the cell-free nucleosome is a mononucleosome, oligonucleosome or other chromosome fragment.

It will be clear to those skilled in the art that the level of isolated tumor nucleosomes as a proportion of nucleosomes present may be used as a measure of the proportion of DNA that comprises tumor DNA in a sample. Furthermore, the converse level is the proportion of DNA of healthy origin in the sample. Therefore, the methods described herein may be used to detect the level/proportion of ctDNA in a sample. Such a measure is similar to allelic frequency measures of cancer associated mutations in ctDNA and may be used as a measure of tumor burden and response to therapy.

In one embodiment of the invention a wholly or partially purified tumor nucleosome preparation is isolated from a sample of a biological fluid. In one embodiment, the purification method involves the affinity isolation of cell free nucleosomes which contain a histone or DNA epigenetic signal epitope characteristic of healthy tissue by employing a binder that binds to the said epigenetic epitope. The elution therefore contains the tumor nucleosome preparation and/or its associated ctDNA which may then be analysed.

Methods of contacting and isolating the nucleosomes from a sample as required herein are well known in the art and any suitable separation method may be used. For example, separation methods may include affinity chromatography or magnetic antibody beads. If using an affinity column chromatography set up, for example, it will be understood that the sample may be passed through an affinity column comprising H1 binding agents. Either the solid phase bound nucleosomes or the flow through (i.e. the unbound nucleosomes) may be collected for analysis of ctDNA depending on whether a positive or negative selection method described herein is employed.

In a preferred embodiment tumor nucleosome and ctDNA isolation is performed by an immunological affinity purification method employing a binder to histone H1. It will be clear to persons skilled in the art that any binding agent capable of specific binding to a histone H1 may be used for affinity purification methods of the invention. Such binding agents may include, without limitation, antibodies, aptamers or binding proteins (e.g.; nucleosome binding proteins).

Antibodies may be raised by a variety of methods known in the art including immunization and library methods such as phage display. The immune response may be induced against, or the library may be selected for binding to, the moiety or antigen of interest. Antibodies directed to bind to histone H1 may be raised against a variety of such moieties including the whole H1 protein amino acid sequence and may optionally contain post-translational histone modifications. The protein may be purified from living cells or produced synthetically. Alternatively, a peptide sequence representing a part of the H1 amino acid sequence may be used and this may also optionally contain post-translational histone modifications. Nucleosomes or other chromatin fractions containing histone H1 may also be used.

It will be clear to those skilled in the art that binding agents directed to bind to any part of, or all of histone H1 may be employed in methods of the invention.

The analysis of the isolated nucleosomes of tumor origin may involve any suitable method of analysis of which many are known in the art. These methods include without limitation analysis by immunoassay using a second antibody or other binder to a common nucleosome epitope such as dsDNA or to an epigenetic structure of interest including a histone modification, histone variant, DNA modification or another molecule adducted to a nucleosome. These methods include herein by reference all the methods described in WO 2005/019826, WO 2013/030577, WO 2013/030579 and WO 2013/084002 wherein a histone H1 binder is employed in place of a general anti-nucleosome epitope binder. These methods also include multiplex methods for the analysis of multiple epitopes present in circulating nucleosomes of tumor origin.

The analysis of nucleosomes of tumor origin isolated by a method of the invention may also involve any proteomics method known in the art including, without limitation, electrophoresis methods, chromatographic methods and any method involving mass spectrometry including methods involving chromatography and mass spectrometry and/or stable isotope labelled mass spectrometry and/or methods involving protein digestion to produce peptides for identification and/or quantification by mass spectrometry or any combinatorial mass spectrometry method with any other method.

In a preferred embodiment of the invention a circulating nucleosome preparation enriched for nucleosomes of tumor origin is prepared by affinity purification of circulating nucleosomes in a blood, serum or plasma sample taken from a cancer patient and the epigenetic composition of the nucleosome preparation is investigated by a method involving mass spectrometry. Therefore, in one embodiment the method comprises the steps of:

(i) contacting the sample with a histone H1 binding agent;
(ii) separating the nucleosome fractions which are free or bound to the histone H1 binding agent and isolating one of the fractions; and
(iii) analyzing the nucleosomes isolated in step (ii) using a method comprising mass spectrometry.

It will be understood by a person skilled in the art that depending on whether the positive or negative selection method described herein is used will determine which nucleosome fraction is isolated (i.e. the bound fraction for the positive selection method or the free/eluted fraction for the negative selection method).

According to a further aspect of the invention, there is provided a method for isolating purified tumor DNA from a biological sample, wherein said method comprises the steps of:
(i) contacting the sample with a histone H1 binding agent;
(ii) isolating nucleosomes which are not bound to the binding agent;
(iii) extracting DNA from the nucleosome sample isolated in step (ii); and
(iv) analysing the extracted DNA.

According to a further aspect of the invention, there is provided a method for isolating purified tumor DNA from a biological sample, wherein said method comprises the steps of:
(i) contacting the sample with a binding agent that binds to histone H1 variant selected from H1.1, H1.2, H1.3, H1.4, H.1.5 or H1.6, or a histone H1 modification;
(ii) isolating nucleosomes which are bound to the binding agent;
(iii) extracting DNA from the nucleosome sample isolated in step (ii); and
(iv) analysing the extracted DNA.

Investigation of purified or isolated tumor DNA may involve analysis of any or all types of cancer associated DNA abnormalities including, without limitation, epigenetic analysis including the methylation of DNA sequences, point mutations, translocations, gene copy number, micro-satellite abnormalities and DNA strand integrity. Further any DNA analysis method may be employed including, without limitation, DNA sequencing, methylated DNA sequencing analysis, PCR, BEAMing, NGS (targeted or whole genome), digital PCR, cold PCR (co-amplification at lower denaturation temperature-PCR), MAP (MIDI-Activated Pyrophosphorolysis), PARE (personalized analysis of rearranged ends) and Mass Spectrometry.

In one embodiment of the methods of the invention, the biological sample is whole blood, blood serum, plasma, cerebrospinal fluid, urine, fecal, sputum, saliva, or other bodily fluid, or breath, condensed breath, or an extract or purification therefrom, or dilution thereof. In a further embodiment, the biological sample is blood, serum or plasma. In a yet further embodiment, the biological sample is serum.

Methods of collection of biological samples are well known in the art and it will be understood that any such methods of collection are suitable for use with the methods described herein.

Further Epigenetic Markers

Once the nucleosomes enriched for tumor origin have been isolated, they may be analysed for further epigenetic markers ("epigenetic epitopes") or subjected to further enrichment methods.

Therefore, according to one aspect of the invention, there is provided an immunoassay method for detecting an epigenetic epitope of tumor derived nucleosomes in a biological sample, wherein said method comprises the steps of:
(i) contacting the sample with a first binding agent that binds to histone H1 or histone H1 variant selected from H1.0, H1.10 or H1.X;
(ii) isolating nucleosomes which are not bound to the first binding agent (i.e. unbound nucleosomes);
(iii) contacting the nucleosomes obtained in step (ii) with a second binding agent which binds to said epitope;
(iv) detecting and/or quantifying the binding of said second binding agent to said epitope; and
(v) using the presence or degree of such binding as a measure of the presence of the particular epitope of tumor derived nucleosomes in the sample.

According to another aspect of the invention, there is provided an immunoassay method for detecting an epigenetic epitope of tumor derived nucleosomes in a biological sample, wherein said method comprises the steps of:
(i) contacting the sample with a first binding agent; that binds to histone H1 variant selected from H1.1, H1.2, H1.3, H1.4, H.1.5 or H1.6, or a histone H1 modification
(ii) isolating nucleosomes which are bound to the first binding agent;
(iii) contacting the nucleosomes obtained in step (ii) with a second binding agent which binds to said epitope;
(iv) detecting and/or quantifying the binding of said second binding agent to said epitope; and
(v) using the presence or degree of such binding as a measure of the presence of the particular epitope of tumor derived nucleosomes in the sample.

In one embodiment, the epitope is selected from a histone modification, a modified nucleotide, a histone variant or isoform, or a nucleosome adduct or variant thereof. In a further embodiment, the epitope comprises a histone modification. In a yet further embodiment, the histone modification comprises H3K27Ac and/or 5-methylcytosine.

A variety of epigenetically modified nucleotides have been described in the literature and epigenetic modification patterns in DNA and/or DNA nucleotide residues are known to be altered in cancer. The best described of these includes methylation of cytosine at position 5. DNA containing 5-methylcytosine is often referred to as "methylated DNA". The methylation of DNA in cancer cells is estimated to be reduced by approximately 50% compared to the DNA of healthy cells (Guerrero-Preston et al, 2007; Soares et al, 1999). However, the cancer associated increase in the level of circulating nucleosomes is reported to be 970% on average (Holdenrieder et al, 2001) and the increase in cfDNA to be about 600% (Schwarzenbach et al, 2011).

Assays for further epigenetic epitopes may be performed in isolation or as part of an assay panel.

In one embodiment, the isolated nucleosome sample obtained from the methods described herein are subject to further enrichment steps. Therefore, in one embodiment, a method of the invention additionally comprises contacting the isolated nucleosomes with a histone H3.1 and/or H3.2 and/or H3t binding agent. It has previously been shown that the histone 3 variants H3.1, H3.2 and H3t, may be used for ctDNA enrichment.

In this embodiment, the method steps may comprise:
(i) contacting the sample with a histone H1 binding agent;
(ii) separating the nucleosome fractions which are free or bound to the histone H1 binding agent and isolating one of the fractions;
(iii) contacting the isolated fraction with a histone H3.1 and/or H3.2 and/or H3t binding agent;
(iv) isolating bound nucleosomes from the sample; and (v) analysing the isolated nucleosomes and/or associated DNA.

It will be appreciated that any of the aforementioned methods may be used either as a stand-alone method or in combination with existing tests.

Methods of Diagnosis

The methods described herein may be used in conjunction with methods of diagnosis. For example, a sample may be enriched to isolate DNA or cell free nucleosomes of tumor origin using the methods described herein and the enriched sample may then be used in a method of diagnosis by detecting further epigenetic markers which are associated with disease.

Therefore, according to a further aspect of the invention, there is provided a method of diagnosing or detecting cancer in an animal or a human subject which comprises the steps of:
  (i) obtaining a biological sample from the subject;
  (ii) contacting the sample with a histone H1 binding agent;
  (iii) separating the nucleosome fractions which are free or bound to the histone H1 binding agent and isolating one of the fractions;
  (iv) contacting the isolated nucleosomes obtained in step (iii) with a second binding agent which binds to an epigenetic epitope of tumor derived nucleosomes;
  (v) detecting and/or quantifying the binding of said second binding agent to said epitope; and
  (vi) using the measured level of biomarker(s) as indicative of the presence of said disease in the subject.

Detecting and/or quantifying may be performed directly on the purified or enriched nucleosome sample, or indirectly on an extract therefrom, or on a dilution thereof. Quantifying the amount of the biomarker present in a sample may include determining the concentration of the biomarker present in the sample. Uses and methods of detecting, monitoring and of diagnosis according to the invention described herein are useful to confirm the existence of a disease, to monitor development of the disease by assessing onset and progression, or to assess amelioration or regression of the disease. Uses and methods of detecting, monitoring and of diagnosis are also useful in methods for assessment of clinical screening, prognosis, choice of therapy, evaluation of therapeutic benefit, i.e. for drug screening and drug development.

The methods of diagnosis described herein may further comprise comparing the level of the second binding agent present in the biological sample with one or more control(s). In one embodiment, the biological sample from the one or more control(s) is taken from healthy (or "normal") patient(s) and/or patient(s) with an associated benign disease. In a further embodiment, the biological sample from the one or more control(s) is taken from healthy patient(s).

As described herein, the methods of the invention can combine the use of two immunoassays. Therefore, according to a further aspect of the invention, there is provided a method for diagnosing or detecting cancer in an animal or a human subject which comprises the steps of:
  (i) obtaining a biological sample from the subject;
  (ii) analyzing the sample for cell free nucleosomes that contain an epigenetic feature and also contain histone H1 by means of an immunoassay using two binding agents, one of which is directed to bind to the particular epigenetic feature and the other of which is directed to bind to histone H1;
  (iii) analyzing the sample for cell free nucleosomes that contain the particular epigenetic feature, both with and without histone H1, by means of an immunoassay using two binding agents, one of which is directed to bind to the epigenetic feature and the other of which is directed to bind to a common core nucleosome epitope including any histone H2, H3 or H4 epitope, any DNA epitope or any other epitope present in chromatin fragments other than a histone H1 epitope; and
  (iv) using a combination of the immunoassay results obtained in steps (ii) and (iii) as a combination biomarker indicative of the presence of said cancer in the subject.

Methods of Treatment

According to a further aspect of the invention, there is provided a method of treating cancer, in an animal or a human subject, which comprises the following steps:
  (i) contacting a biological sample obtained from the subject with a histone H1 binding agent;
  (ii) separating the nucleosome fractions which are free or bound to the histone H1 binding agent and isolating one of the fractions;
  (iii) contacting the isolated nucleosomes obtained in step (ii) with a second binding agent which binds to an epitope of tumor derived nucleosomes;
  (iv) detecting and/or measuring the level of binding of said second binding agent to said epitope;
  (v) using the measured level of biomarker(s) in step (iv) as indicative of the presence of said disease in the subject; and
  (vi) treating surgically or administering a therapeutic agent to a subject diagnosed in step (v) as a patient having said disease.

As described herein, it will be clear which fraction is isolated depending on the histone H1 binding agent used and whether a negative or positive selection method is required.

As described herein, the methods of the invention can combine the use of two immunoassays. Therefore, according to a further aspect of the invention, there is provided a method for treating cancer, in an animal or a human subject, which comprises the following steps:
  (i) obtaining a biological sample from the subject;
  (ii) analyzing the sample for cell free nucleosomes that contain an epigenetic feature and also contain histone H1 by means of an immunoassay using two binding agents, one of which is directed to bind to the particular epigenetic feature and the other of which is directed to bind to histone H1;
  (iii) analyzing the sample for cell free nucleosomes that contain the particular epigenetic feature, both with and without histone H1, by means of an immunoassay using two binding agents, one of which is directed to bind to the epigenetic feature and the other of which is directed to bind to a common core nucleosome epitope including any histone H2, H3 or H4 epitope, any DNA epitope or any other epitope present in chromatin fragments other than a histone H1 epitope;
  (iv) using the measured level of biomarker(s) in steps (ii) and (iii) as indicative of the presence of said cancer in the subject; and
  (v) treating surgically or administering a therapeutic agent to a subject diagnosed in step (iv) as a patient having said cancer.

The methods described herein may further comprise comparing the level of the biomarker(s) present in the biological sample with one or more control(s). In one embodiment, the biological sample from the one or more control(s) is taken from healthy (or "normal") patient(s) and/or patient(s) with an associated benign disease. In a further embodiment, the biological sample from the one or more control(s) is taken from healthy patient(s).

Therefore, according to a further aspect of the invention, there is provided a method of treating cancer in an individual in need thereof, which comprises the step of administering a therapeutic agent to a patient identified as having differing levels of the biomarker(s) as defined herein in a biological sample when compared to the levels of said biomarker(s) in a biological sample obtained from a control subject.

In one embodiment, the cancer is selected from: breast, bladder, colorectal, skin (such as melanoma), ovarian, prostate, lung, pancreatic, bowel, liver, endometrial, lymphoma, oral, head and neck cancer, leukaemia and osteosarcoma.

Therapeutic agents and methods of surgery used for treating said diseases are well known to a person skilled in the art. Methods of treatment for cancer include, but are not limited to, surgery, chemotherapy, radiotherapy or other therapeutic agents (such as drugs or biological therapies, such as monoclonal antibodies).

Uses

According to a further aspect of the invention, there is provided a use of a histone H1 binding agent for detecting, isolating and/or purifying cell free nucleosomes of tumor origin from a biological sample. Alternatively, according to a further aspect of the invention, there is provided a use of a histone H1 binding agent for detecting, isolating and/or purifying cell free nucleosomes from healthy tissue from a biological sample. As described herein, the presence or absence of histone H1 or the presence of certain histone H1 variants and modifications have been associated with cell free nucleosomes originating from tumors or healthy tissue, therefore histone H1 binding agents may be used as a biomarker to detect said nucleosomes.

In one embodiment, the cell free nucleosomes are isolated and/or purified.

Kits

According to a further aspect of the invention, there is provided the use of a kit comprising a histone H1 binding agent in any of the methods described herein.

It will be understood that the embodiments described herein may be applied to all aspects of the invention, Furthermore, all publications, including but not limited to patents and patent applications, cited in this specification are herein incorporated by reference as though fully set forth.

The invention will now be illustrated with reference to the following non-limiting examples.

Example 1

An antibody directed to bind specifically to histone H1 variant H1.0, H1.10 or H1.X is biotinylated and immobilized on streptavidin coated magnetic beads (Dynal) by the recommended method of the manufacturer. The beads are washed several times with loading buffer using a magnetic separation system. Serum or plasma taken from a cancer patient is diluted in loading buffer and added to the beads. Nucleosomes originating in healthy cells containing the histone H1 variant are adsorbed to the beads. Nucleosomes of tumor origin (which do not contain the histone H1 variant) remain in solution. The beads are removed by means of magnetic separation to leave a solution of nucleosomes of tumor origin. Nucleosome associated ctDNA is extracted by the phenol/chloroform method or other standard extraction methods. The extracted DNA may be analysed for genetic or epigenetic features of cancer.

Example 2

An antibody directed to bind specifically to histone H1 variant H1.0, H1.10 or H1.X is immobilized on a solid support to produce an affinity purification chromatography column by the recommended method of the solid phase manufacturer. Serum or plasma taken from a cancer patient is diluted in loading buffer and added to the column. Nucleosomes originating in healthy cells containing the histone H1 variant are adsorbed to the column. Nucleosomes of tumor origin (which do not contain the histone H1 variant) remain in solution and pass through the column and are collected as eluate. Nucleosome associated ctDNA is extracted by the phenol/chloroform method or other standard extraction methods. The extracted DNA may be analysed for genetic or epigenetic features of cancer.

Example 3

A solution of nucleosomes of tumor origin is isolated using a solid phase immobilized anti-H1 variant antibody as in EXAMPLE 1, or EXAMPLE 2. The isolated nucleosomes present in solution are analysed by immunoassay or by proteomics methods including Mass Spectroscopy.

Example 4

An antibody directed to bind specifically to histone H1 variant H1.1, H1.2, H1.3, H1.4, H1.5 or H1.6 is biotinylated and immobilized on streptavidin coated magnetic beads (Dynal) by the recommended method of the manufacturer. The beads are washed several times with loading buffer using a magnetic separation system. Serum or plasma taken from a cancer patient is diluted in loading buffer and added to the beads. Nucleosomes of tumor origin containing the histone H1 variant are adsorbed to the beads. The beads are isolated from the solution by means of magnetic separation. Nucleosome associated ctDNA is extracted by the phenol/chloroform method or other standard extraction methods from the solid phase beads. The extracted DNA may be analysed for genetic or epigenetic features of cancer.

Example 5

An antibody directed to bind specifically to histone H1 variant H1.1, H1.2, H1.3, H1.4, H1.5 or H1.6 is immobilized on a solid support to produce an affinity purification chromatography column by the recommended method of the solid phase manufacturer. Serum or plasma taken from a cancer patient is diluted in loading buffer and added to the column. Nucleosomes of tumor origin containing the histone H1 variant are adsorbed to the column. Nucleosomes of healthy cellular origin (which do not contain the histone H1 variant) remain in solution and pass through the column. The column is washed and nucleosome associated ctDNA is extracted by the phenol/chloroform method or other standard extraction methods. The extracted DNA may be analysed for genetic or epigenetic features of cancer.

Example 6

A preparation of solid phase bound nucleosomes of tumor origin is isolated using a solid phase anti-H1 variant as in EXAMPLE 4 or EXAMPLE 5. The isolated nucleosomes are analysed by immunoassay or by proteomics methods including Mass Spectroscopy.

Example 7

An antibody directed to bind specifically to histone H1 per se is biotinylated and immobilized on streptavidin coated magnetic beads (Dynal) by the recommended method of the manufacturer. The beads are washed several times with loading buffer using a magnetic separation system. Serum or plasma taken from a cancer patient is diluted in loading buffer and added to the beads. Nucleosomes containing histone H1 are adsorbed to the beads. The nucleosomes of tumor origin (containing no histone H1) remain in solution. The beads are isolated from the solution by means of magnetic separation. Once the beads have been removed, the isolated nucleosomes present in solution are analysed by immunoassay or by proteomics methods including Mass Spectroscopy.

Example 8

An antibody directed to bind specifically to histone H1 per se is immobilized on a solid support to produce an affinity purification chromatography column by the recommended method of the solid phase manufacturer. Serum or plasma taken from a cancer patient is diluted in loading buffer and added to the column. Nucleosomes containing the histone H1 are adsorbed to the column. The nucleosomes of tumor origin (containing no histone H1) remain in solution and pass through the column. The solution of nucleosomes of tumor origin is collected as eluate. The isolated nucleosomes present in solution are analysed by ELISA or by proteomics methods including Mass Spectroscopy

Example 9

A solution of nucleosomes of tumor origin is prepared as in EXAMPLE 7 or EXAMPLE 8. Nucleosome associated ctDNA is extracted form solution by the phenol/chloroform method or other standard extraction methods. The extracted DNA may be analysed for genetic or epigenetic features of cancer.

Example 10

Nucleosomes of tumor origin in a body fluid sample taken from a subject are isolated using a solid phase immobilized anti-H1 antibody as in any of examples EXAMPLE 1-9. The isolated nucleosomes and/or associated DNA present in solution are analysed by methods known in the art.

Example 11

An antibody directed to bind specifically to histone H1 per se, or to a histone H1 variant, is biotinylated and immobilized on streptavidin coated magnetic beads (Dynal) by the recommended method of the manufacturer. The beads are washed several times with loading buffer using a magnetic separation system. Serum or plasma taken from a cancer patient is diluted in loading buffer and added to the beads. Nucleosomes originating in healthy cells containing the histone H1 variant are adsorbed to the beads. Nucleosomes of tumor origin (which do not contain the histone H1 variant) remain in solution. The beads are removed by means of magnetic separation to leave a solution of nucleosomes predominantly of tumor origin. The solution of tumor nucleosomes is then assayed for methylated DNA using an ELISA method for nucleosome associated nucleotide 5-methylcytosine using a solid phase anti-histone H2, H3 and/or H4 epitope or anti-nucleosome capture antibody that binds intact nucleosomes and a biotinylated monoclonal anti-5-methylcytosine detection antibody as follows: A solution of anti-histone H2, H3 or H4 antibody in 0.1M phosphate buffer pH 7.4 is added to microtitre wells (100 µL/well) and incubated overnight at 4° C. to coat the wells with capture antibody. Excess anti-histone antibody is decanted. A solution of bovine serum albumin (20 g/L) is added to the wells (200 µL/well) and incubated 30 minutes at room temperature to block excess protein binding sites on the wells. Excess bovine serum albumin solution was decanted and the wells were washed three times with wash buffer (200 µL/well, 0.05M TRIS/HCl buffer pH 7.5 containing 1% Tween 20). Sample (10 µL/well) and assay buffer (50 µL/well, 0.05M TRIS/HCl pH 7.5 containing 0.9% NaCl, 0.05% sodium deoxycholate and 1% Nonidet P40 substitute) are added to the wells incubated 90 minutes at room temperature with mild agitation. The sample and assay buffer mixture is decanted and the wells are washed three times with wash buffer (200 µL/well). A solution of biotinylated anti-5-methylcytosine detection antibody is added (50 µL/well) and incubated 90 minutes at room temperature with mild agitation. Excess detection antibody is decanted and the wells are again washed three times with wash buffer (200 µL/well). A solution containing a streptavidin-horse radish peroxidase conjugate is added (50 µL/well) and incubated 30 minutes at room temperature with mild agitation. Excess conjugate is decanted and the wells are again washed three times with wash buffer (200 µL/well). A coloured substrate solution (100 µL/well, 2,2'-Azinobis [3-ethylbenzothiazoline-6-sulfonic acid]-diammonium salt) is added and incubated 20 minutes at room temperature with mild agitation. The optical density (OD) of the wells was measured at a wavelength of 405 nm using a standard microtitre plate reader. A dose response curve of increasing colour with increasing nucleosome associated anti-5-methylcytosine concentration is observed with a low background signal observed in the absence of 5-methylcytosine (fetal calf serum). The positive ELISA signal indicates that the 5-methylcytosine detected by the ELISA is incorporated within intact nucleosomes comprising both histone protein, but not histone H1, and DNA as (i) nucleosomes containing histone H1 have been removed by affinity purification, (ii) the capture antibody binds to histone H2, H3 and/or H4 epitopes in the sample and (iii) detection antibody binds to the 5-methylcytosine component of DNA.

Example 12

Nucleosomes of tumor origin in a body fluid sample taken from a subject are isolated using a solid phase immobilized anti-H1 antibody as in EXAMPLE 11. The isolated nucleosomes are analysed by the ELISA method described in EXAMPLE 11, but using a biotinylated monoclonal anti-modified histone detection antibody; for example an antibody directed to bind to H3K9(Me)3.

Example 13

Nucleosomes of tumor origin in a body fluid sample taken from a subject are isolated using a solid phase immobilized anti-H1 antibody as in EXAMPLE 11. The isolated nucleosomes are analysed by the ELISA method described in EXAMPLE 11, but using a biotinylated monoclonal anti-histone isoform detection antibody; for example an antibody directed to bind to H2AZ.

Example 14

Nucleosomes of tumor origin in a body fluid sample taken from a subject are isolated using a solid phase immobilized anti-H1 antibody as in EXAMPLE 11. The isolated nucleosomes are analysed by the ELISA method described in EXAMPLE 11, but using a biotinylated monoclonal directed to bind to a non-histone protein adducted to an isolated circulating cell free nucleosome; for example an antibody directed to bind to the androgen receptor. The results show that cell free nucleosomes of tumor origin adducted to the protein concerned are present in the blood circulation (or other body fluid) of the subject.

Example 15

Serum samples were obtained from 29 healthy subjects, 29 subjects diagnosed with colorectal cancer and 11 subjects diagnosed with pancreatic cancer. Plastic microtiter wells were coated with an antibody directed to bind to a non-histone chromatin protein and blocked according to standard procedures. An antibody directed to bind to histone H1 per se and an antibody directed to bind to a common core histone present on all or most nucleosomes were labelled by biotinylation. Two immunoassays were carried out on each sample.

In the first immunoassay; sample (10 μL/well) and assay buffer (50 μL/well, 0.05M TRIS/HCl pH 7.5 containing 0.9% NaCl, 0.05% sodium deoxycholate and 1% Nonidet P40 substitute) were added to the wells incubated 90 minutes at room temperature with mild agitation. The sample and assay buffer mixture were decanted and the wells washed three times with wash buffer (200 μL/well). A solution of biotinylated anti-histone H1 detection antibody was added (50 μL/well) and incubated 90 minutes at room temperature with mild agitation. Excess detection antibody was decanted and the wells again washed three times with wash buffer (200 μL/well). A solution containing a streptavidin-horse radish peroxidase conjugate was added (50 μL/well) and incubated 30 minutes at room temperature with mild agitation. Excess conjugate was decanted and the wells again washed three times with wash buffer (200 μL/well). A coloured substrate solution (100 μL/well, 2,2'-Azinobis [3-ethylbenzothiazoline-6-sulfonic acid]-diammonium salt) was added and incubated 20 minutes at room temperature with mild agitation. The optical density of immunoassay 1 (OD1) of the wells was measured at a wavelength of 405 nm using a standard microtitre plate reader. All measurements were performed in duplicate and a mean result used.

In the second immunoassay; sample (10 μL/well) and assay buffer (50 μL/well, 0.05M TRIS/HCl pH 7.5 containing 0.9% NaCl, 0.05% sodium deoxycholate and 1% Nonidet P40 substitute) were added to the wells incubated 90 minutes at room temperature with mild agitation. The sample and assay buffer mixture were decanted and the wells washed three times with wash buffer (200 μL/well). A solution of biotinylated anti-core nucleosome detection antibody was added (50 μL/well) and incubated 90 minutes at room temperature with mild agitation. Excess detection antibody was decanted and the wells again washed three times with wash buffer (200 μL/well). A solution containing a streptavidin-horse radish peroxidase conjugate was added (50 μL/well) and incubated 30 minutes at room temperature with mild agitation. Excess conjugate was decanted and the wells again washed three times with wash buffer (200 μL/well). A coloured substrate solution (100 μL/well, 2,2'-Azinobis [3-ethylbenzothiazoline-6-sulfonic acid]-diammonium salt) was added and incubated 20 minutes at room temperature with mild agitation. The optical density of immunoassay 2 (OD2) of the wells was measured at a wavelength of 405 nm using a standard microtitre plate reader. All measurements were performed in duplicate and a mean result used.

For each sample the ratio OD2:OD1 was calculated. The OD2:OD1 ratio results for all 69 subjects are shown in FIG. 1. For the 29 healthy subjects the mean immunoassay ratio found was 8.7. For the 29 subjects diagnosed with colorectal cancer the mean ratio was 15.9. For the 11 subjects diagnosed with pancreatic cancer the mean ratio was 17.1. This demonstrates that an increasing ratio was associated with nucleosomes of cancer origin.

Moreover, the individual results for each subject were used as a biomarker for cancer with increasing cut-off levels. At a cut-off of 12; the ratio gave a positive result for 73% (8 of 11) of subjects diagnosed with pancreatic cancer and 41% (12 of 29) of subjects diagnosed with colorectal cancer at a clinical specificity of 79% (6 false positive results among 29 healthy subjects). At a cut-off of 22; the ratio gave a positive result for 36% (4 of 11) of subjects diagnosed with pancreatic cancer and 34% (10 of 29) of subjects diagnosed with colorectal cancer at a clinical specificity of 93% (2 false positive results among 29 healthy subjects). The results in FIG. 1 show that the methods described herein can be used to detect cancer. These results also demonstrate that combined immunoassay results as described herein can be used as a combination biomarker for cancer diseases.

REFERENCES

Crowley et al, Nature Reviews Clinical Oncology, 10, 472-484, 2013.
Fong et al, Clinical Chemistry 55(3), 587-589, 2009.
Grutzmann et al, PLoS ONE 3(11): e3759. doi:10.1371/journal.pone.0003759, 2008.
Guerrero-Preston et al, Epigenetics 2(4), 223-226, 2007.
Holdenrieder et al, Int J Cancer 95, 114-120, 2001.
Holdenrieder and Stieber, Critical Reviews in Clinical Laboratory Sciences; 46(1): 1-24, 2009.
Izzo and Schneider, (2015) Biochimica et Biophysica Acta S1874-9399 (15) 189-3
Jung et al, Clinica Chimica Acta, 411, 1611-1624, 2010.
Karczarski et al, Clinical Proteomics, 11:24, 2014.
Newman et al, Nature Medicine 20(5), 548-554, 2014.
Scaffidi, (2015) BBA—Gene Reg. Mechanisms: doi: 10.1016/j.bbagrm.2015.09.008
Schwarzenbach et al, Nature Reviews Cancer, 11(6), 426-437, 2011.
Soares et al, Cancer 85(1), 112-118, 1999.
Zhou et al, Seminars in Oncology, 39(4), 440-448, 2012.

The invention claimed is:
1. A method for analysing cell free nucleosomes of tumor origin from a biological sample by affinity purification wherein said method comprises the steps of:
    (i) contacting the sample with a histone H1 binding agent;
    (ii) isolating nucleosomes from the sample which are not bound to the histone H1 binding agent; and
    (iii) analysing the isolated nucleosomes by immunoassay or mass spectroscopy.

2. The method of claim 1, wherein the histone H1 binding agent is selected from: a binding agent that binds to histone H1 protein, variant, isoform or modification thereof.

3. The method of claim 1, wherein the histone H1 binding agent is selected from: a binding agent that binds to histone H1 protein or a histone H1 variant selected from H1.0, H1.10 or H1.X.

4. The method of claim 1, wherein the isolated nucleosomes are analysed by immunoassay or mass spectroscopy for inclusion of an epigenetic feature selected from: a post-translational histone modification, a histone isoform, a modified nucleotide or an adducted non-histone protein.

5. The method according to claim 1, wherein the step of analysing the isolated nucleosomes comprises an immunoassay.

6. The method according to claim 1, wherein the step of analysing the isolated nucleosomes comprises mass spectrometry.

7. A method for isolating purified tumor DNA from a biological sample, wherein said method comprises the steps of:
   (i) contacting the sample with a histone H1 binding agent;
   (ii) isolating nucleosomes which are not bound to the histone H1 binding agent;
   (iii) extracting DNA from the nucleosome sample isolated in step (ii); and
   (iv) analysing the extracted DNA.

8. The method according to claim 7, wherein the step of analysing the extracted DNA comprises: DNA sequencing, methylated DNA sequencing analysis, PCR, BEAMing, NGS (targeted or whole genome), digital PCR, cold PCR (co-amplification at lower denaturation temperature-PCR), MAP (MIDI-Activated Pyrophosphorolysis), PARE (personalized analysis of rearranged ends) or Mass Spectrometry.

9. The method of to claim 1, which additionally comprises contacting the isolated nucleosomes with a histone H3.1 and/or H3.2 and/or H3t binding agent.

10. An immunoassay method for detecting an epigenetic epitope of tumor derived nucleosomes in a biological sample, wherein said method comprises the steps of:
    (i) contacting the sample with a first binding agent comprising a histone H1 binding agent;
    (ii) isolating nucleosomes which are not bound to the first binding agent;
    (iii) contacting the nucleosomes with a second binding agent which binds to said epitope;
    (iv) detecting and/or quantifying the binding of said second binding agent to said epitope; and
    (v) using the presence or degree of such binding as a measure of the presence of the particular epitope of tumor derived nucleosomes in the sample.

11. The method according to claim 10, wherein the epitope comprises a histone modification.

12. The method according to claim 11, wherein the histone modification comprises H3K27Ac and/or 5-methylcytosine.

13. The method according to claim 10, wherein the epitope comprises a modified nucleotide.

14. The method according to claim 10, wherein the epitope comprises a histone H2A, H2B, H3 or H4 variant or isoform.

15. The method according to claim 10, wherein the epitope comprises a nucleosome adduct or variant thereof.

16. The method according to claim 1, wherein the biological sample comprises blood, serum, plasma, menstrual blood, cerebrospinal fluid (CSF), endometrial fluid, urine, saliva, or other bodily fluid (stool, tear fluid, synovial fluid, sputum), breath, condensed breath, or an extract or purification therefrom, or dilution thereof.

17. The method of claim 16, wherein the biological sample comprises a blood, serum or plasma sample.

18. The method of claim 7, which additionally comprises contacting the isolated nucleosomes with a histone H3.1 and/or H3.2 and/or H3t binding agent.

19. The method according to claim 7, wherein the biological sample comprises blood, serum, plasma, menstrual blood, cerebrospinal fluid (CSF), endometrial fluid, urine, saliva, or other bodily fluid (stool, tear fluid, synovial fluid, sputum), breath, condensed breath, or an extract or purification therefrom, or dilution thereof.

20. The method according to claim 10, wherein the biological sample comprises blood, serum, plasma, menstrual blood, cerebrospinal fluid (CSF), endometrial fluid, urine, saliva, or other bodily fluid (stool, tear fluid, synovial fluid, sputum), breath, condensed breath, or an extract or purification therefrom, or dilution thereof.

* * * * *